United States Patent [19]
Huebner

[11] Patent Number: 5,456,685
[45] Date of Patent: Oct. 10, 1995

[54] INTERFERENCE SCREW HAVING A TAPERED BACK ROOT

[75] Inventor: Randall J. Huebner, Beaverton, Oreg.

[73] Assignee: Smith & Nephew Dyonics, Inc., Memphis, Tenn.

[21] Appl. No.: 196,720

[22] Filed: Feb. 14, 1994

[51] Int. Cl.⁶ .......................... A61B 17/58; A61B 17/86
[52] U.S. Cl. ..................... 606/73; 411/426; 411/395; 411/311
[58] Field of Search ................... 606/73; 411/426, 411/395, 308, 309, 310, 311

[56] References Cited

U.S. PATENT DOCUMENTS

| 3,701,372 | 10/1972 | Breed | 411/309 |
|---|---|---|---|
| 4,468,200 | 8/1984 | Munch | 606/73 |
| 4,537,185 | 8/1985 | Stednitz | 606/73 |
| 4,632,100 | 12/1986 | Somers et al. | |
| 4,772,286 | 2/1987 | Goble et al. | 623/13 |
| 4,870,957 | 10/1989 | Goble et al. | |
| 4,927,421 | 5/1990 | Goble et al. | 606/73 |
| 4,950,270 | 8/1990 | Bowman | 606/72 |
| 5,211,647 | 5/1993 | Schmieding | 606/104 |
| 5,226,766 | 7/1993 | Lasner | 606/73 |
| 5,252,016 | 10/1993 | Schmid et al. | 411/426 |

OTHER PUBLICATIONS

Arthrex, *The Arthrex Transtibial ACL Reconstruction System*, pp. 1–32.
Bach, Jr., B. R., *Potential Pitfalls of Kurosaka Screw Interference Fixation for ACL Surgery*, The American Journal of Knee Surgery, vol. 2, No. 2, Apr. 1989, pp. 76–82.
Howemedia, *Specialty Screws*.
Ivey, Marty and Li, Fan, *Tensile Strength of Soft Tissue Fixations About the Knee*, The American Journal of Knee Surgery, vol. 4, No. 1, Jan., 1991, pp. 18–23.
Kurosaka, M., *A Biomechanical Comparison of Different Surgical Techniques of Graft Fixation in Anterior Cruciate Ligament Reconstruction*, The American Journal of Sports Medicine, vol. 15, No. 3, 1987, pp. 225–229.
Kurasaka, M., *Interference Fixation Screw System*.
Matthews, L. S., *Pitfalls in the Use of Interference Screws for Anterior Cruciate Ligament Reconstruction: Brief Report*, The Journal of Arthroscopic and Related Surgery, vol. 5, No. 3, Raven Press, Ltd, 1989, pp. 225–226.

Primary Examiner—Tamara L. Graysay
Assistant Examiner—Scott B. Markow
Attorney, Agent, or Firm—Pravel, Hewitt, Kimball & Krieger

[57] ABSTRACT

An dual tapered orthopedic fixation screw is used to anchor ligament grafts inside a bore in a bone mass. The fixation screw includes a root portion having a front section, a cylindrical center section and a back section. A screw thread is formed over substantially the entire root portion to increase purchase. A taper is formed on the back of the root portion to increase compression of the fixation screw against the ligament graft. The screw further includes a rounded portion that is formed between the taper and the back end of the root to prevent the screw from fraying or cutting the ligament.

18 Claims, 4 Drawing Sheets

INTERFERENCE SCREW HAVING A TAPERED BACK ROOT

BACKGROUND OF THE INVENTION

This invention relates generally to apparatus for securing bone and ligament grafts to a bone mass and more particularly to an orthopedic fixation screw for holding the graft inside a bore.

The anterior cruciate ligament (ACL) is frequently injured in contact sports and other activities. Such injuries cause instability in the knee to an extent that ACL reconstruction may be required.

In ACL reconstruction, a substitute ligament or graft is attached to the distal femur or proximal tibia to facilitate regrowth and permanent attachment. Various methods of graft attachment are known, such as staples and sutures, however, such attachment methods are often not strong enough to withstand normal stress placed on the ligament.

One method for increasing the strength of the graft attachment comprises wedging an interference screw between a graft bone block and an interior wall of a bore formed though the bone mass. Although interference screws are stronger than other ligament attachment methods, such as staples, the sharp outer edges of the screw often cut or fray the ligament after the screw is fixated inside the bore.

U.S. Pat. No. 5,211,647 to Schmieding describes a sheath used for protecting a ligament graft during the insertion process of an interference screw. The sheath contains a cutout portion that enables the interference screw to be exposed to the tunnel wall of the bone during insertion, while at the same time covering the side of the screw facing the graft. The interference screw contains a rounded back section to further reduce the effects of graft cutting.

Because there are no threads at the back end, the screw shown in Schmieding has reduced purchase over fully threaded screws of comparable size. Reduced purchase in the screw increases the chance that the ligament graft may slip in the bore. Further, the screw in Schmieding has a cylindrical root portion that provides only nominal compression of the graft against the inside wall of the bore.

A constant root diameter also exhibits substantially constant resistance when inserted by a surgeon into the bore. Thus, it is hard for the surgeon to physically gauge exactly how far the interference screw has been inserted into the bore. For example, it is important that the screw is not inserted too far past the back end of the bore, while at the same time important that the screw does not extend partially out of the bore after completion of the installation process. The screw in Schmieding, however, gives no physical indication that insertion is near completion.

Accordingly, a need remains for a high purchase interference screw that will not cut or fray an attached ligament graft.

SUMMARY OF THE INVENTION

It is, therefore, an object of the invention to increase the purchase of interference screws.

Another object of the invention is to reduce fraying or cutting effects caused by interference screws on bone and ligament grafts.

A further object of the invention is to increase the strength in which grafts can be attached to a bone mass.

An orthopedic fixation screw contains a specially shaped root portion that anchors bone grafts more securely inside bores in a bone mass. The screw is less likely to cut a ligament graft and also provides a positive positional indication to a surgeon when inserting the screw inside the bore.

The screw includes a root portion having a front and back end. The root portion includes a front section, a cylindrical center section and a back section. A screw thread is formed over substantially the entire root portion for increased purchase capacity.

A taper is formed on the back section to increase compression against the graft. The screw further includes a rounded portion formed between the taper and the back end of the root that prevents the ligament from being cut or frayed after the screw is fully inserted.

The thread maintains a uniform crest diameter along the back and middle sections. The crest of the thread also has a top face that increases in width toward the back end of the root portion. The root portion can either be cannulated for receiving insertion guide wires or can have a solid center with a rounded front end.

The foregoing and other objects, features and advantages of the invention will become more readily apparent from the following detailed description of a preferred embodiment of the invention which proceeds with reference to the accompanying drawings.

DETAILED DESCRIPTION

Figures 1, 2:
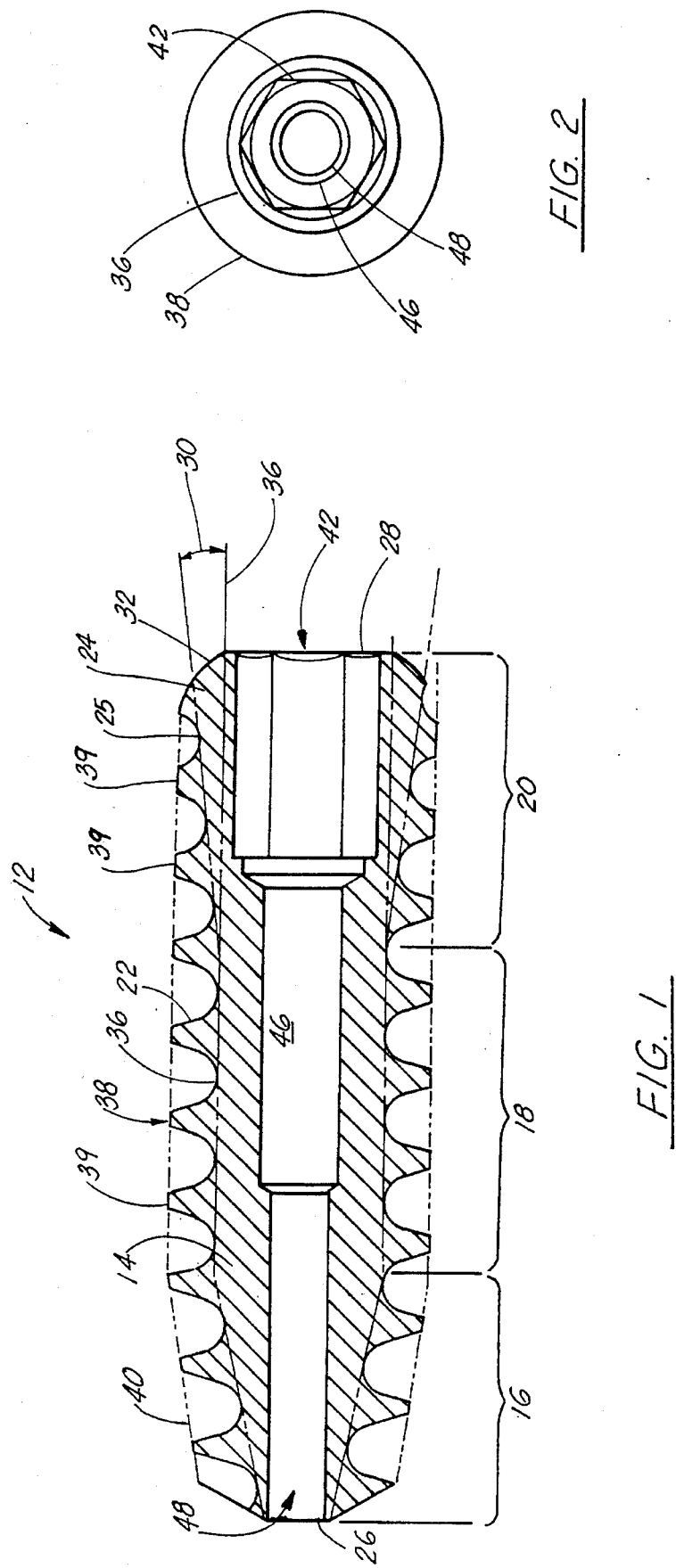
FIG. 1 is a side section view of a fixation screw according to the invention.
FIG. 2 is a rear view of the fixation screw shown in FIG. 1.

FIG. 1 is a side section view of an orthopedic fixation screw 12 according to the invention. The fixation screw 12 has a elongated root portion 14 with a circular cross sectional shape. The root portion 14 includes a front end 26 and a back end 28 and is generally defined by a front section 16, a center section 18 and a back section 20. A thread 22 is formed over substantially the entire root portion 14 from the front end 26 to the back end 28.

A taper 24 is formed on the back section 20 between the back end 28 and the center section 18. The taper 24 includes an outside surface 25 that extends laterally out from the root portion 14 at an angle 30. The angle 30 of outside face 25 makes the taper larger toward the back end 28 than toward the center section 18. In one embodiment, the outside surface 25 of taper 24 has an slope of approximately 7 degrees in relation to an outside surface 36 of root 14. A rounded portion 32 is formed between the taper 24 and the back end 28 of root 14.

The center section 18 has a cylindrically shape. The front section 16 is tapered from the front end 26 to the center section 18 and has a larger diameter toward the center section 18 than toward the front end 26. The front, center and back sections of the root portion 14 each have substantially the same length.

The thread 22 includes a crest 38 that extends a given height above the outside surface 36 of root 14. The crest height diminishes between the center section 18 and the back end 28 inversely to the slope 30 of taper 24. Thus, a substantially uniform crest diameter 40 is maintained along the back section 20 and middle section 18. The crest diameter 40 narrows slightly along the front of the screw in proportion to the taper on front section 16. The crest 38 includes a top face or outer surface 39 that increases in width toward the back end of the root as is shown in FIG. 3.

In one embodiment, the root portion 14 is cannulated for receiving guides wires that direct the screw to a desired mounting position. Referring both to FIG. 1 and to the back view of the fixation screw 12 shown in FIG. 2, the cannulated root portion 14 includes a hexagonal socket 42 for engaging a screw driver (not shown). A center channel section 46 and a front channel section 48 each have circular cross sectional shapes that combine to extend through the center section 18 and front section 16, respectively.

Figure 3:
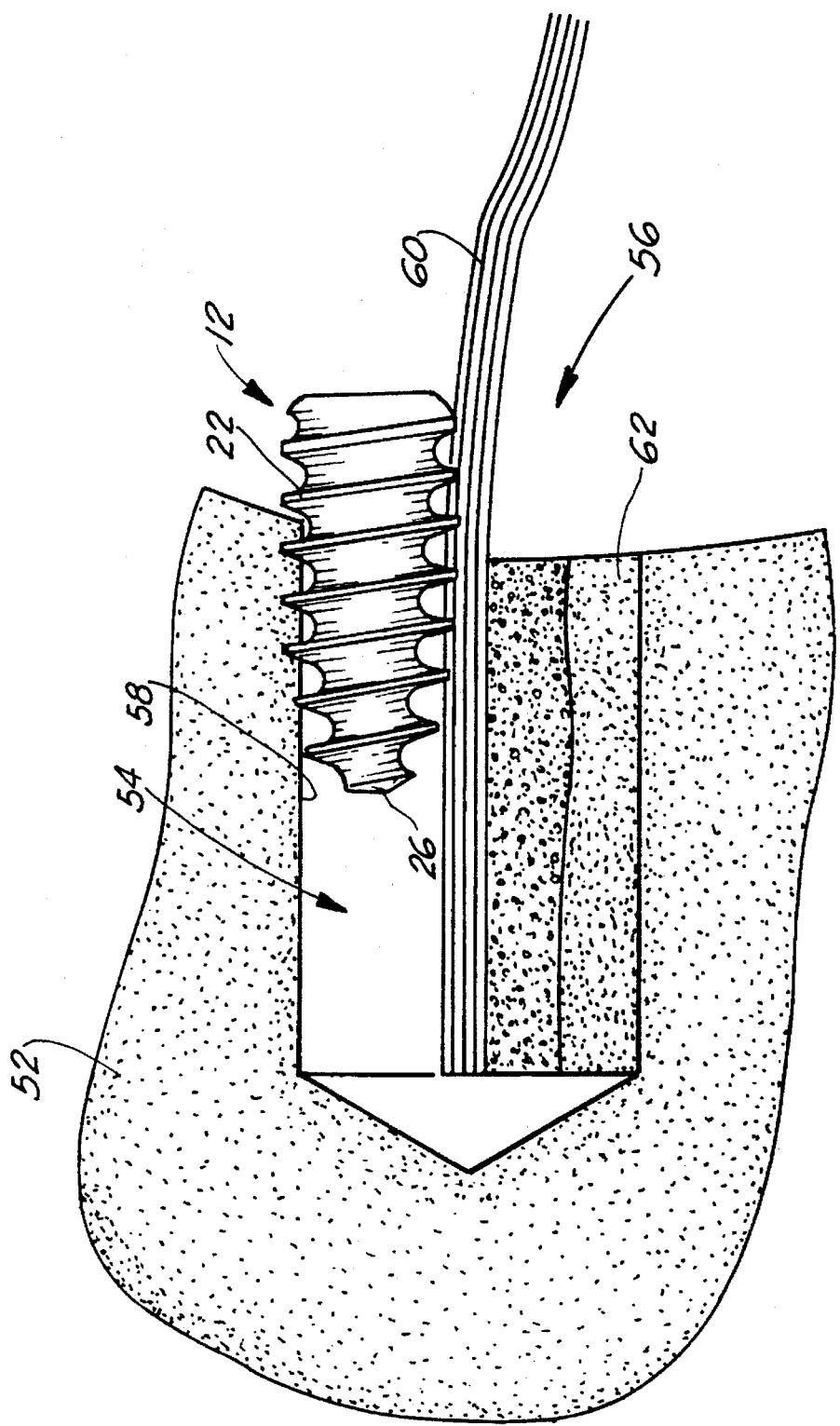
FIG. 3 is a side section view of the fixation screw shown in FIG. 1 partially inserted into a bore between an interior wall of a bone mass and a ligament graft.

FIG. 3 is a side section view of the fixation screw 12 in FIG. 1 shown partially inserted into a bore 54. In the case of ACL reconstructive surgery, the bore is formed in the distal femur or proximal tibia, or both. Screw 12 is used to anchor a bone-tendon graft 56 inside bore 54 which is also referred to as an endosteal tunnel. Graft 56 includes a tendon 60 and a bone portion 62.

An orthopedic surgeon drills into bone mass 52 using a convention orthopedic drill and which may be done endoscopically. After bore 54 is drilled as shown in FIG.3, one end of graft 56 is positioned in the bore as illustrated. Screw 12 is fitted onto a driver (not show) by inserting a hexagonal front end of the driver into socket 42 (FIG. 1). The surgeon grasps the driver and positions the front end 26 of screw 12 between an interior wall 58 of bone mass 52 and tendon 60.

The surgeon pushes the driver axially toward screw 12 while at the same rotating the driver. The threads 22 in turn engage both the inner wall 58 and ligament 60. As the front end of screw 12 advances further into the space between ligament 60 and wall 58, the tapered front section 16 (FIG. 1) gradually compresses graft 56 and bone portion 62 against the opposite side of bore 54. Compression against graft 56 is steadily increased as screw 12 is inserted further into bore 54. The screw 12 is inserted until the back section 20 (FIG. 1) reaches the front of bore 54 as shown in FIG. 3.

Figure 4:
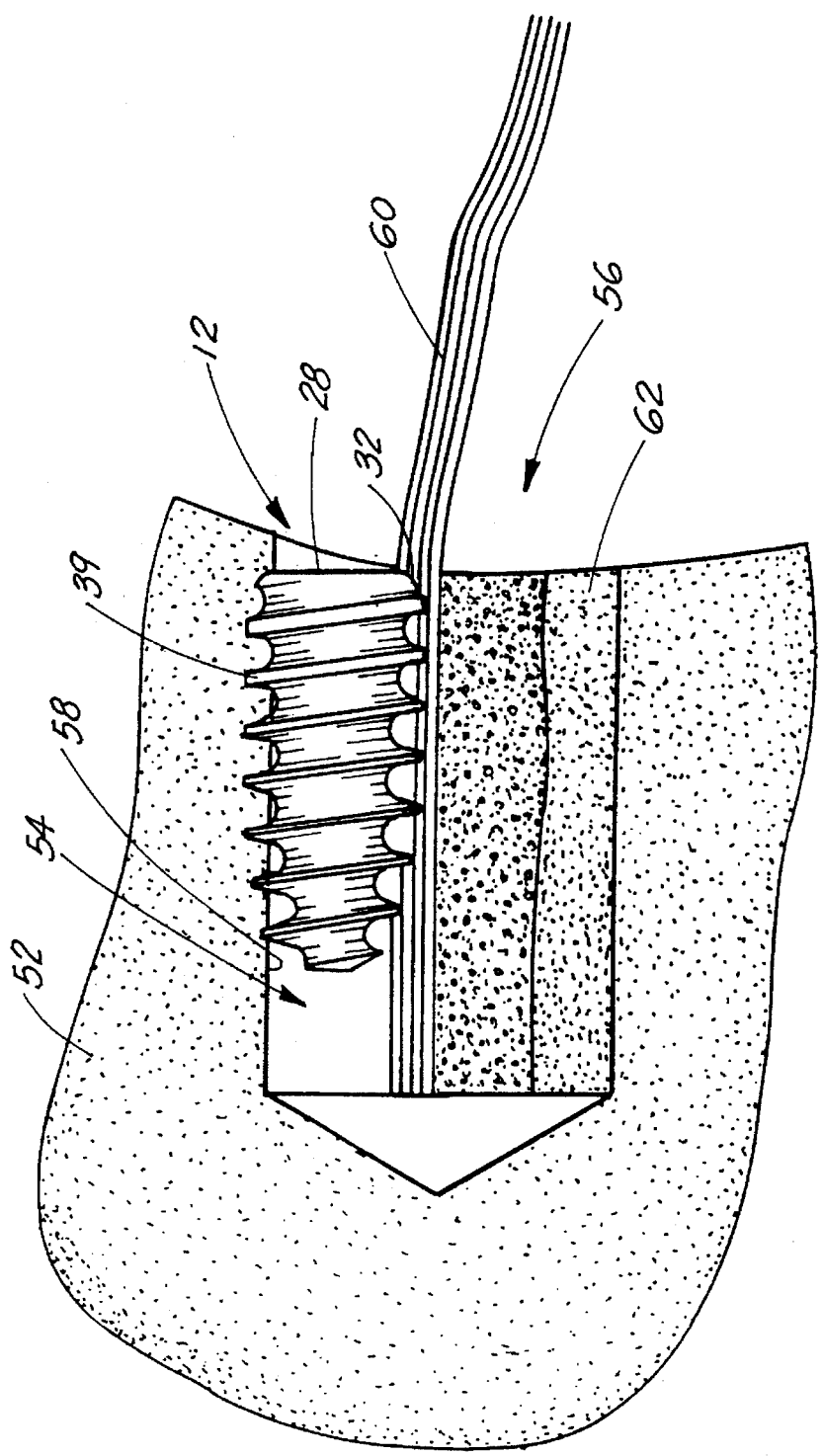
FIG. 4 is the side section view of FIG. 3 with the fixation screw fully inserted into the bore.

Referring to FIG. 4, as the tapered back section 20 begins insertion into bore 54, the rate in which the screw 12 compresses against graft 56 increases. More force is thereby required by the surgeon to further insert the remaining portion of screw 12 into bore 54. The added resistance from screw 12 gives the surgeon positive feedback as to how far the screw is presently inserted into bore 54. The taper 24 on the back portion of root 14 also increases purchase over standard cylindrical roots. Thus, screw 12 holds graft 56 more securely inside bore 54 than other screws of comparable size.

The top face or outer surface 39 increases in width toward the back of screw 12. Each turn of crest 38 thereby cuts a wider groove into wall 58 than the proceeding turn. The threads in the back of screw 12 will then not sit loosely in grooves previously bored by proceeding threads. Thus, each thread is held firmly in bone mass 52 further reducing the possibility of screw 12 coming loose.

The tapered front root section 16 allow the threads 22 to gain purchase at a relatively narrow portion of the root in turn reducing shifting or twisting of graft 56 during installation. Therefore, it is not necessary to provide a cannulated root portion 22 and guide wires that would normally be used to prevent screw divergence during installation.

Screw 12 is further inserted until the back end 28 is fully seated inside bore 54 as illustrated in FIG. 4. The rounded portion 32 of screw 12 prevents cutting or fraying of ligament 60 when ligament 60 is flexed during regular leg movements. Once the screw 12 is positioned as shown in FIG. 4, the surgeon withdraws the driver from socket 42.

Figure 6:
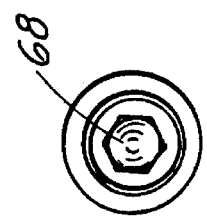
FIG. 6 is a rear view of the fixation screw shown in FIG. 5.
Figure 5:
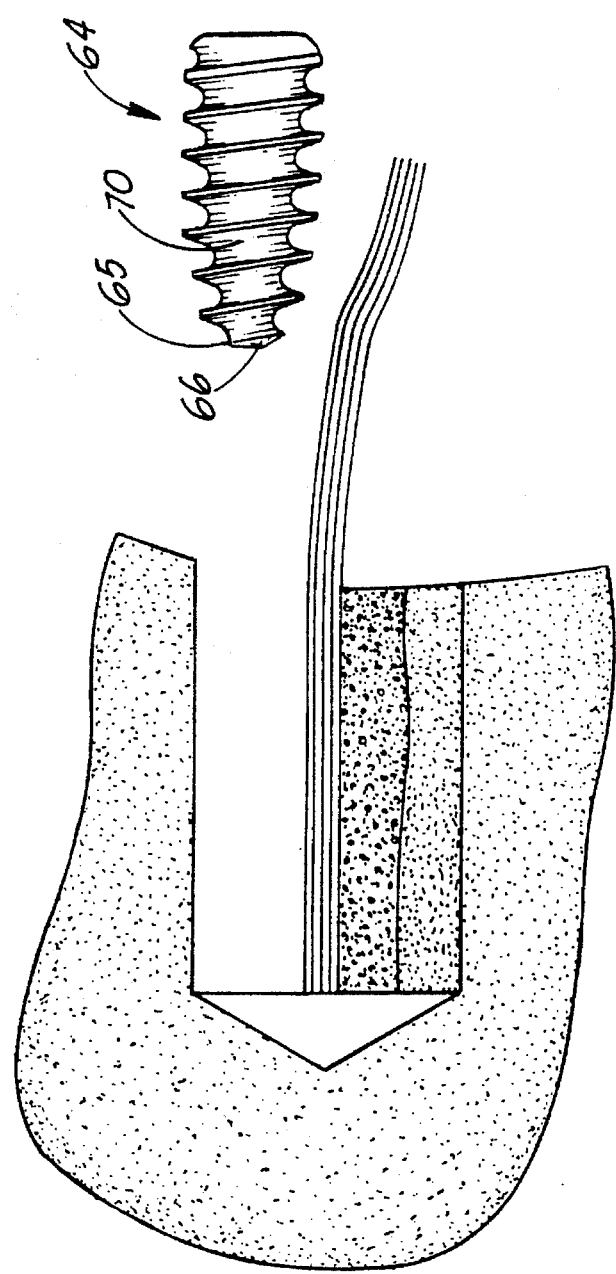
FIG. 5 is an alternative embodiment of the fixation screw according to the invention having a solid root portion.

FIG. 5 shows a screw 64 having a solid root portion 70. FIG. 6 is a back view of the fixation screw 64 showing a hexagonal socket 68 for receiving a driver (not shown). Screw 64 includes the same tapers in the front and back sections of the root portion 70. A rounded portion 66 is located at a front end 65.

Having described and illustrated the principles of the invention in a preferred embodiment thereof, it should be apparent that the invention can be modified in arrangement and detail without departing from such principles. I claim all modifications and variation coming within the spirit and scope of the following claims.

I claim:

1. An orthopedic interference screw for compression anchoring a bone graft in a bore formed in a bone mass, said screw comprising:

a root having front and back ends and further including at least a center section and a back section; the root center section and back section having an outer surface a screw thread formed over substantially all of the center and back sections, the screw thread including a crest with a top face having a width that increases at least along the back section away from the center section; and a taper formed on said root back section and extending substantially entirely between said back end and said center section, said taper being larger toward the back end than toward the center section.

2. The screw of claim 1, wherein the root back end includes an outer surface, the back end outer surface having a rounded edge between said back end outer surface and the outer surface of the root back section.

3. The screw of claim 2, wherein said root further includes a front section having a taper, said front section taper extending substantially entirely along the front section, such that the front section root diameter decreases away from the center section.

4. The screw of claim 2, wherein the screw thread crest extends above the outer surface of the root, the distance between the screw thread crest and the outer surface of the root along the center section is substantially constant, and the root diameter is substantially constant along the center section, thereby maintaining a substantially uniform diameter across the thread along the center section of the root.

5. The screw of claim 4, wherein the distance between the screw thread crest and the outer surface of the root along substantially the entire back section diminishes toward the back end.

6. The screw of claim 5, wherein the distance between the screw thread crest and the outer surface of the root along the back root section diminishes inversely to said taper, thereby maintaining a substantially uniform diameter across the thread along the back section of the root.

7. The crew of claim 6, wherein said root further includes a front section having a taper, said front section taper extending substantially entirely along the front section, such that the front section root diameter decreases away from the center section.

8. The screw of claim 7, wherein the root is cannulated.

9. The screw of claim 1, wherein the distance between the screw thread crest and the root along the center section is substantially constant, and the root diameter is substantially constant along the center section, thereby maintaining a substantially uniform diameter across the thread along the center section of the root.

10. The screw of claim 9, wherein the distance between the screw thread crest and the outer surface of the root along substantially the entire back section diminishes toward the back end.

11. The screw of claim 10, wherein the distance between the screw thread crest and the outer surface of the root along the back root section diminishes inversely to said taper, thereby maintaining a substantially uniform diameter across the thread along the back section of the root.

12. The screw of claims 1, wherein the root is cannulated.

13. An orthopedic interference screw for compression anchoring a bone graft in a bore formed in a bone mass, said screw comprising:

a root having a front end, back end, a front section, a center section and a back section;

a screw thread formed over substantially all of the front, center and back sections, the screw thread including a crest with an outer surface having a width that increases at least along the back section away from the center section; and a taper formed on said root back section and extending substantially entirely between said back end and said center section, said taper being larger toward the back end than toward the center section.

14. The screw of claim 13, wherein the front and back sections are substantially the same length.

15. The screw of claim 13, wherein the taper has a slope of approximately 7 degrees.

16. The screw of claim 13, wherein the screw further includes a channel extending longitudinally through the entire root, the channel having a hexagonal socket in the back section for engaging a driver and a substantially circular cross-section in the center and front sections.

17. The screw of claim 13, wherein the root further includes a front end and the screw further includes a rounded nose joined to the front end.

18. The screw of claim 1 or 13, wherein the outer surface of the screw thread crest comprises a flat face.

* * * * *